(12) United States Patent
Chu (10) Patent No.: US 7,335,155 B2
(45) Date of Patent: Feb. 26, 2008

(54) UNITARY FORMULATION DELIVERY DEVICE

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 275 days.

(21) Appl. No.: 10/940,274

(22) Filed: Sep. 14, 2004

(65) Prior Publication Data

US 2006/0058569 A1    Mar. 16, 2006

(51) Int. Cl.
*A61M 36/00*    (2006.01)
(52) U.S. Cl. .......................................................... 600/7
(58) Field of Classification Search ................ 600/1–8; 604/59–60, 57
See application file for complete search history.

(56) References Cited

U.S. PATENT DOCUMENTS

| | | | |
|---|---|---|---|
| 2,883,984 A | 4/1959 | Candido, Jr. et al. | |
| 4,908,017 A | 3/1990 | Howson et al. | 604/67 |
| 6,007,515 A | 12/1999 | Epstein et al. | 604/82 |
| 6,053,899 A | 4/2000 | Slanda et al. | 604/500 |
| 6,102,896 A | 8/2000 | Roser | 604/218 |
| 6,142,972 A * | 11/2000 | Cheikh | 604/57 |
| 7,041,048 B2 * | 5/2006 | Drobnik et al. | 600/7 |
| 2003/0171718 A1 * | 9/2003 | DeLegge et al. | 604/164.01 |
| 2005/0038312 A1 * | 2/2005 | Green et al. | 600/7 |
| 2005/0070821 A1 * | 3/2005 | Deal et al. | 600/585 |
| 2005/0080468 A1 * | 4/2005 | Christman | 607/96 |

FOREIGN PATENT DOCUMENTS

| | | |
|---|---|---|
| WO | WO 97/22379 | 6/1997 |
| WO | WO 02/085188 A2 | 10/2002 |

* cited by examiner

*Primary Examiner*—Charles A. Marmor, II
*Assistant Examiner*—Christine D. Hopkins
(74) *Attorney, Agent, or Firm*—Mayer & Williams PC; David B. Bonham, Esq.; Keum J. Park, Esq.

(57) ABSTRACT

An apparatus for delivering a formulation into a body in integer amounts includes
a cannula with an insertion end for insertion into the body. The cannula includes a channel such as a tube to store the formulation. A rod is inserted into an end of the cannula opposite the insertion end; the rod has one end to contact the formulation and another end. The actuator controllably moves the rod through the tube of the cannula to deliver the formulation through the insertion end of the cannula.

20 Claims, 6 Drawing Sheets

FIG 6

UNITARY FORMULATION DELIVERY DEVICE

FIELD OF THE INVENTION

The present invention relates generally to methods and apparatuses for delivering medicine or other materials into a body, and more particularly, to a method and apparatus for delivering medicine or other material in solid, gaseous or liquid form into the body.

BACKGROUND

Prostate diseases such as prostatitis, benign prostatic hypertrophy, prostatodynia, and prostate carcinoma afflict many adult males. The largest segment of the population of men stricken with prostate problems includes those over age fifty. However, inherited prostate problems can appear in much younger men.

Benign prostatic hypertrophy (BPH) is a condition where the prostate over-grows or becomes enlarged. Prostate growth is controlled by androgen receptors found in the prostate gland. It is generally believed that when the androgen receptors are stimulated by 5-alpha-dihydrotesterone (DHT), they cause the prostate to grow. DHT is produced by an enzymatic conversion of testosterone in the prostate.

Over the past twenty years a variety of approaches have been developed to treat benign prostatic hypertrophy. In general, these approaches alter the prostatic tissue volume or the biochemistry of the prostate, and they include the application of heat, cold, chemical agents, pharmaceutical agents and radiation. In recent years, a number of minimally invasive technologies have been developed, including radiation, RF ablation, microwave ablation, cryogenic ablation/freezing, and chemo-ablation. Chemo-ablative approaches, including injection of alcohol or salt solutions, have been evaluated for the treatment of benign prostatic hypertrophy. However, the lack of delivery control when administering ablative liquids has led to unpredictable retention of the same, leading to nonspecific ablation of both the prostate as well as surrounding tissues and organs.

The present invention is therefore directed to the problem of developing a method and apparatus for delivering formulations in a controlled manner into the human body, for example, into prostatic tissue, including chemotherapy to treat BPH and brachytherapy to treat prostate cancer, as well as periurethral delivery of bulking agents to treat stress urinary incontinence (SUI), and the delivery of other localized drug/therapeutic formulations to treat other benign or malignant tissue conditions in other areas of the body.

SUMMARY OF THE INVENTION

The present invention solves these and other problems by providing a delivery method and device for injecting formulations of solids, liquids or gases in integer amounts into the body of a human.

According to one aspect of the present invention, an exemplary embodiment of a method for delivering a solid formulation into the human body injects the solid formulation into the body via a single needle insertion, while enabling repositioning of the insertion device to another body location to inject additional solid formulation without total removal of the needle from the body for reloading.

According to another aspect of the present invention, an exemplary embodiment of a method for delivering solid formulation to a human body provides for storage of a supply of the solid formulation within the delivery device.

According to another aspect of the present invention, the methods and apparatus for delivering solid or semi-solid (e.g., a gel) formulations to the body can be employed to inject salt or sodium chloride formulations into the prostrate to necrosis tissue for the treatment of BPH. Moreover, other ablation/necrosing or other therapeutic agents can be used with the methods and apparatus of the present invention, including but not limited to acids, bases, enzymes, and paclitaxel.

Another potential application of the methods and apparatus of the present invention include delivering radioactive seeds, for example, in connection with brachytherapy to treat prostate cancer; delivering bulking agents, for example, to treat stress urinary incontinence; and delivering other localized drug/therapeutic formulations to treat other benign/malignant tissue conditions in other areas of the body.

Still another potential application of the methods and apparatus of the present invention include endoscopic procedures, in which case the delivery device is supplied with a flexible needle or cannula used in endoscopic procedures. The delivery device can also be fitted through rigid or flexible scopes.

Still another potential application of the methods and apparatus of the present invention includes ultrasonic probes or other devices using a guide sheath or other adaptive means.

Other aspects of the present invention will be apparent upon review of the following drawings in light of the detailed description.

DETAILED DESCRIPTION

The present invention now will be described more fully hereinafter with reference to the accompanying drawings, in which preferred embodiments of the invention are shown. This invention may, however, be embodied in different forms and should not be construed as limited to the embodiments set forth herein.

Figure 1:
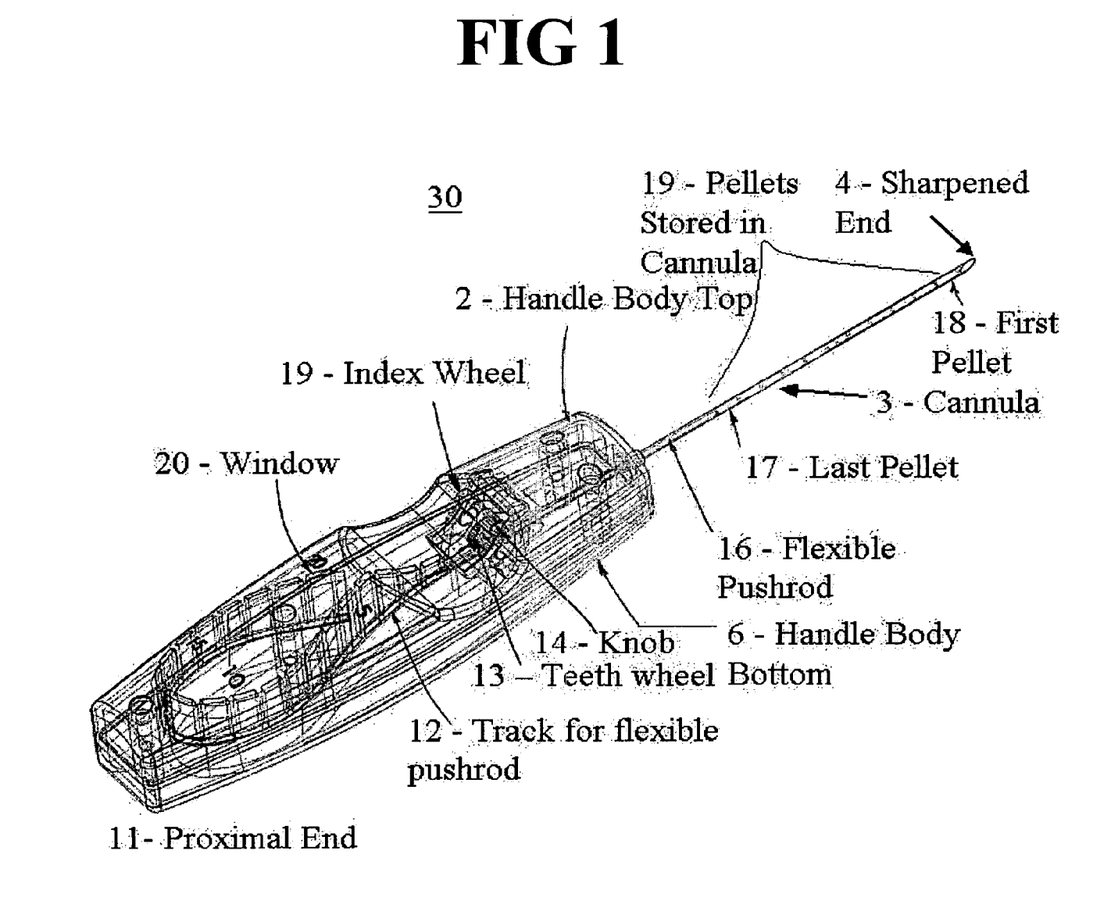
FIG. 1 depicts an exemplary embodiment of an apparatus for delivering integer amounts of a formulation into a body according to one aspect of the present invention.

Turning to FIG. 1, shown therein is a see-through view or wire frame diagram of an exemplary embodiment of a delivery device 30 according to one aspect of the present invention. At the distal end (opposite the proximal end 11), the cannula 3 stores pellets 19 end to end, abutted to each other or stacked in a column within the lumen. The first pellet 18 to be injected is closest to the sharpened end 4 of the cannula 3 while the last pellet 17 is abutted to the flexible pushrod 16, which can have a variety of cross-sections including circular, oval, square, rectangular, and so forth.

While solid pellets are shown, the pellets can also be used for delivering a liquid or a gas (e.g., within a dissolvable shell of the pellet).

A flexible pushrod 16 is sized to fit within the inner diameter of the cannula 3 and extends into a curved track 12 formed by the top 2 and bottom 6 of the handle body. The pushrod 16 is preferred to be of a mechanically robust material, such as metal or plastic. Example materials include round nitinol or nylon, which are flexible and have columnar strength, but the invention is not limited to these exemplary materials. The pushrod 16 may also be coated with a soft plastic material.

Figure 3:
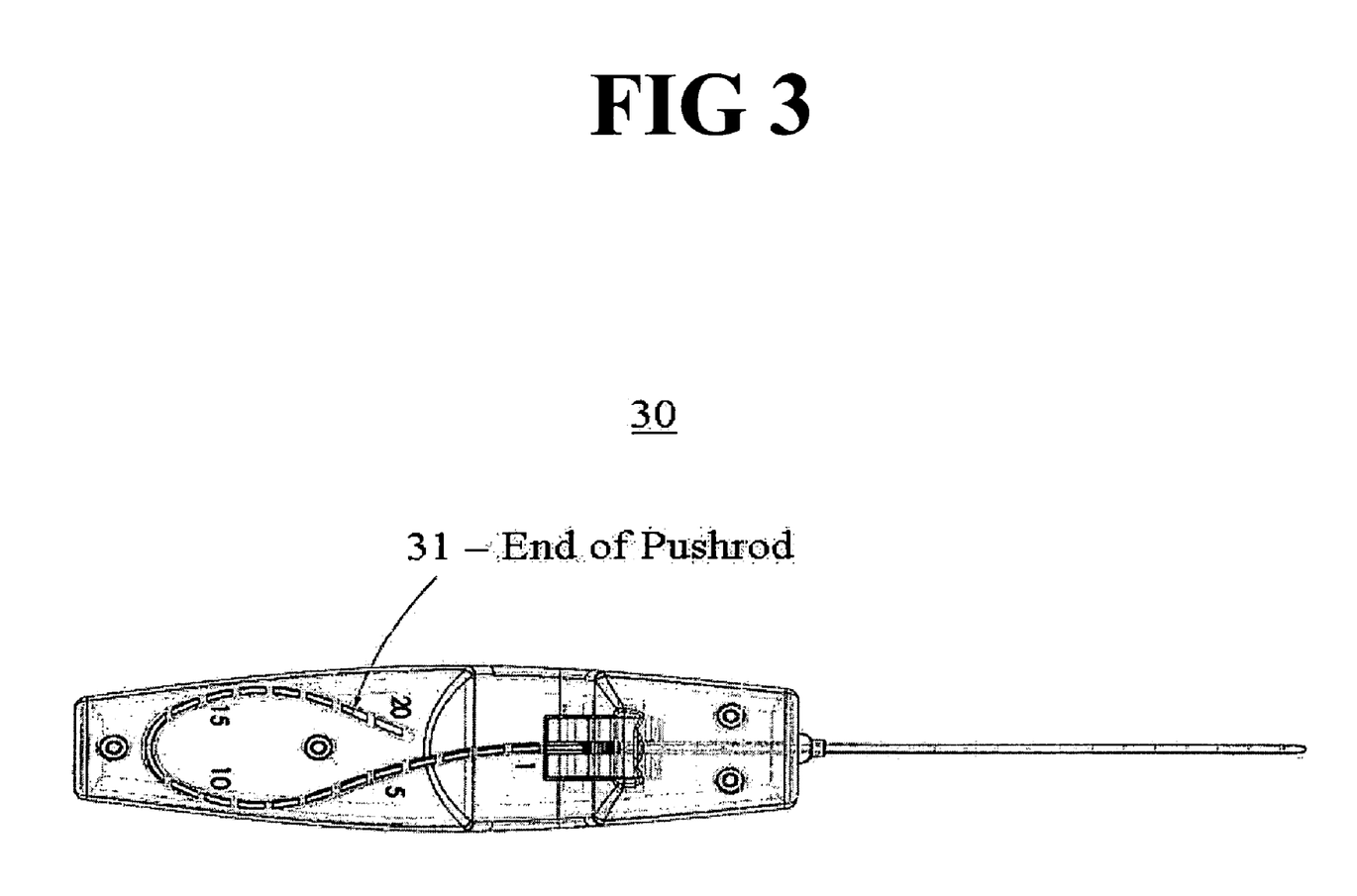
FIG. 3 depicts a top view of the embodiment of FIG. 1.

The length of the pushrod 16 in this case is such that one end of the pushrod 16 abuts to the last pellet 17 and the other end of the pushrod 16 can be seen through window 20 (see also FIG. 3, element 31). Each of the rectangular windows can be numbered from 1 through 20. While a 20 pellet capacity is shown, the pellet loading could be more or less, depending upon the desired application, dosage form and concentration. The track 12 of the flexible rod 16 is lined with windows and labeled 20, 15, 10 and 1 to indicate the number of pellets remaining. All of the windows could be so labeled; however, they are not labeled to simplify the figure. In use, as the pushrod 16 is advanced, the window showing the end 31 of the pushrod 16 indicates the number of pellets remaining.

Also shown in FIG. 1 is an index wheel 19 that rotates about an axis used to advance the pushrod 16 in the length increment of the pellets. The particular index wheel 19 shown in FIG. 1 is designed to dispense one pellet for a quarter turn. The index wheel 19 consists of four knobs 14 (see also FIG. 2, element 22) and a wheel with teeth 13 to engage the pushrod 16 against the bottom track at all times. When using a liquid or a gas, the incremental rotation of the index wheel will dispense a measured amount of the liquid or gas equal to the volume of a pellet, or the volume of the cannula that the pushrod moves through during each movement. In this case, the cannula configuration would be slightly different to account for closing the end when using a gas or liquid. For example, the distal end would be closed and valving employed. In contrast, with a semi-solid or solid pellet, the cannula can employ an open end so the pellet is simply pushed out.

Figure 2:
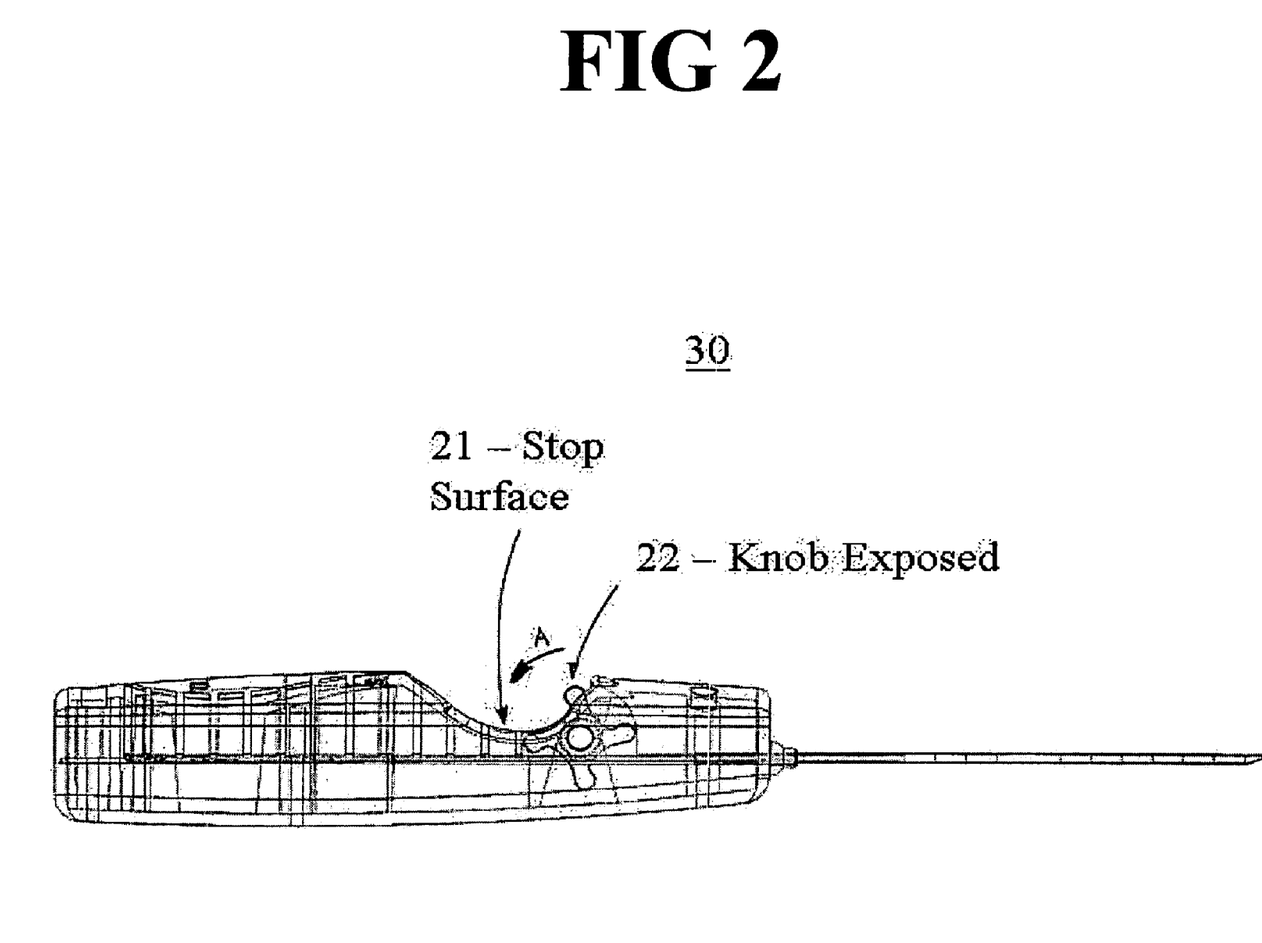
FIG. 2 depicts a side view of the embodiment of FIG. 1.

Turning to FIG. 2, shown therein is a side view of the embodiment 30 from FIG. 1. To dispense a single pellet, the exposed knob 22 from the top handle body is rotated in direction of arrow A with the thumb until the stop surface 21 is met. This action causes the teeth wheel 13 to rotate a quarter turn or translating the movement of the pushrod 16 to the length of one pellet. All of the pellets move distally the same distance causing the most distal pellet to extend beyond the cannula tip 4 to be dispensed. In the same activation motion the next knob is rotated into the exposed position ready to be activated. If preferred the next pellet can be dispensed consecutively in that location (without manual reloading or removal of the delivery device 30 from the body for reloading and then repositioning to the same location for dispensing). If also preferred, the cannula 3 can be partially withdrawn and/or re-positioned to another location to dispense another pellet without reloading or total withdrawal to minimize injury or needle paths into an organ or tissue.

FIG. 3 shows a top view of the embodiment 30, in which one pellet has been dispensed and 19 pellets remain, indicated by the end 31 of the pushrod 16 in window 19 (which is the window next to window 20).

Figure 4:
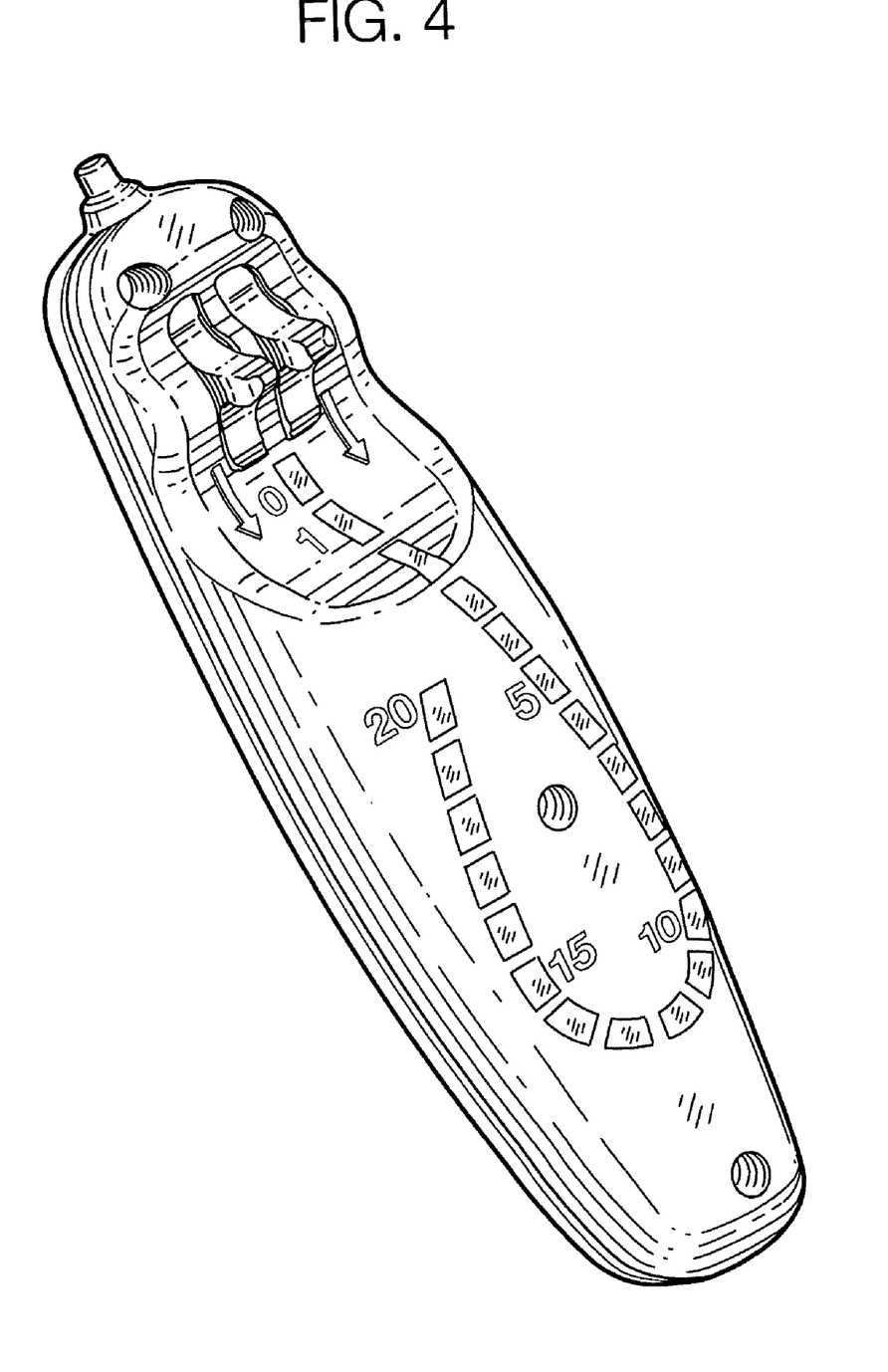
FIG. 4 depicts another exemplary embodiment of an apparatus for delivering formulations into a body according to another aspect of the present invention.

FIG. 4 shows another exemplary embodiment of an apparatus for delivering formulation into the body. In this embodiment, the needle or cannula is not shown attached to the body.

Figure 5:
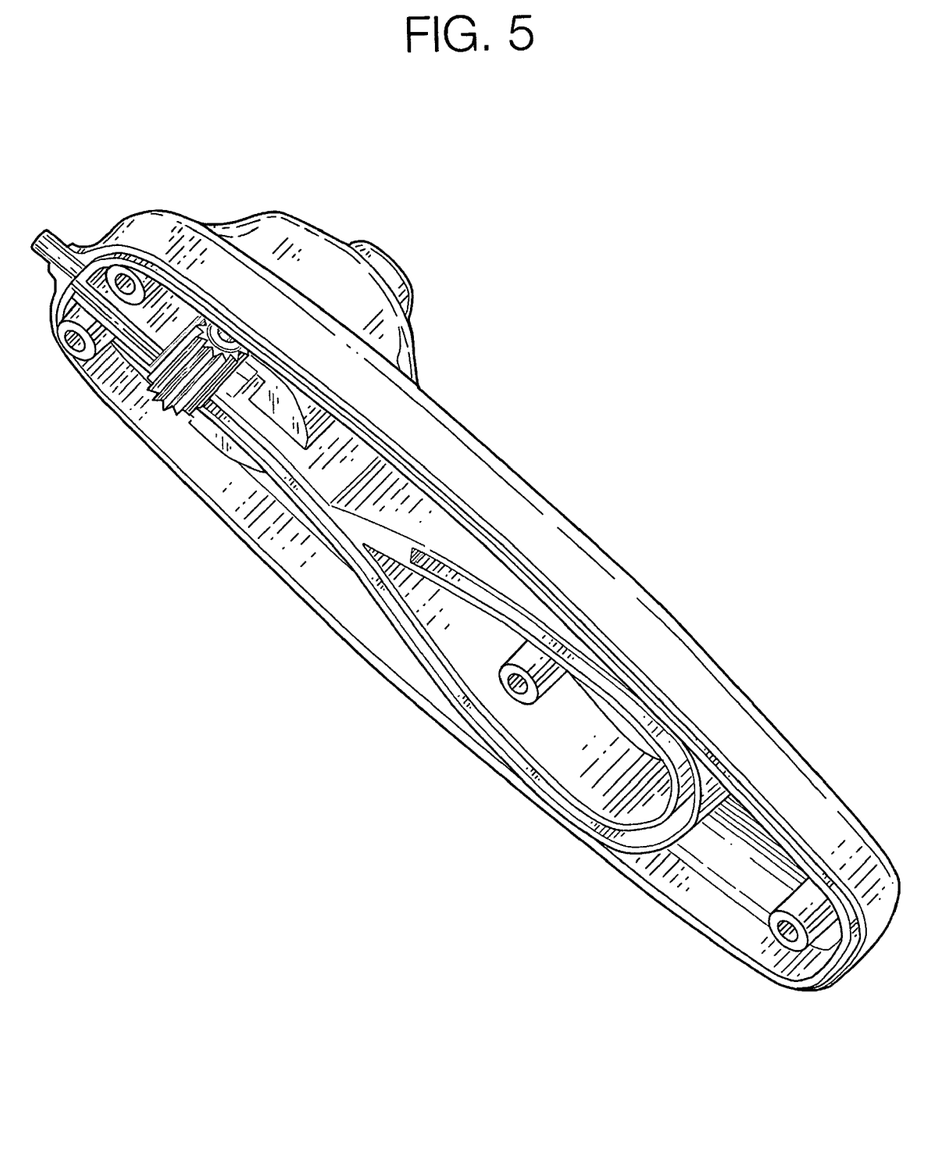
FIGS. 5-6 depict yet another exemplary embodiment of an apparatus for delivering formulations into a body according to still another aspect of the present invention.
Figure 6:
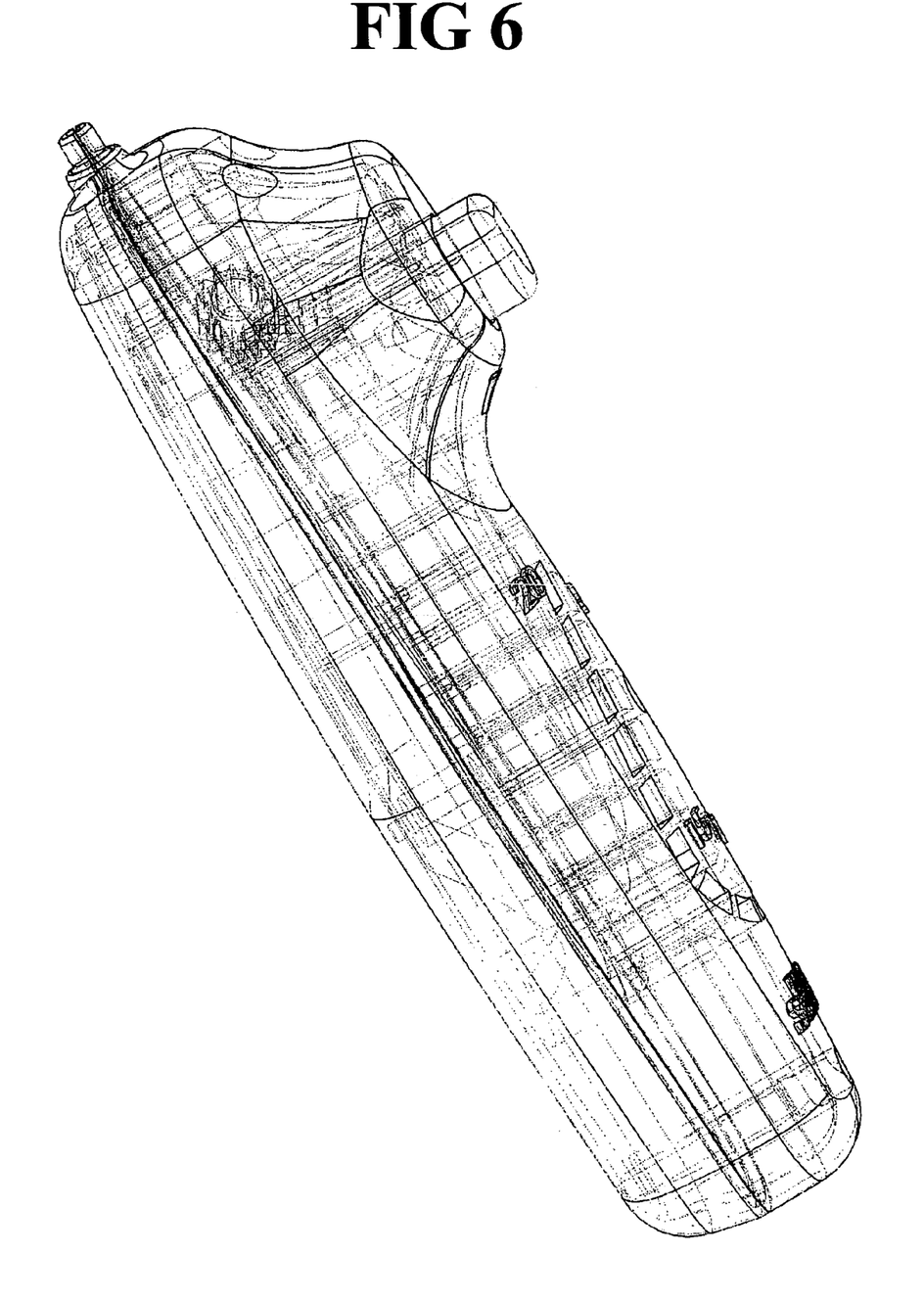

FIGS. 5-6 depict yet another exemplary embodiment of an apparatus for delivering formulations into the body. In this embodiment, the user actuator comprises a push button rather than a knob or wheel as shown in the other embodiments.

In another exemplary embodiment, the pellets are replaced with radioactive seeds for brachytherapy.

In still another exemplary embodiment, the needle or cannula has an echogenic tip with markings to be used with ultrasound or fluoroscopy. Other external grid guides or external or internal imaging (e.g., MRI, ultrasound, direct scope visualization, and so forth) can be used to aid placement of the needle or dispensing agent.

In yet another exemplary embodiment, the needle is flexible and sized to be used in a working channel of a scope, such as an endoscope.

According to another aspect of the present invention, the pellet shape can be cylindrical, spherical, a rectangular parallelepiped, a cuboid, a semiregular polyhedron, a convex polyhedron, a prism, a wedge or any other preferred shape.

According to still another aspect of the present invention, the pellet can be composed of any preferred material. The composition of the pellet, however, should be sufficient to withstand the pressure being placed on each pellet so that when being pushed by the flexible pushrod damage to the pellet does not occur, but rather movement of the pellet through the cannula occurs.

According to still another aspect of the present invention, the index wheel can be designed to rotate in increments of 1, ½, ⅓, ¼, ⅛ or any other desired ratio.

According to still another aspect of the present invention, the pellet indication windows can be replaced with a dial or counter.

According to still another aspect of the present invention, the pellet can be liquid, solid, gas or drug filled capsules. The capsules can be dissolvable.

According to still another aspect of the present invention, the pellets can be shaped with a point for easier penetration into tissue.

According to still another aspect of the present invention, the pushrod can be colored or striped for clearer visibility.

According to still another aspect of the present invention, the teeth wheel can be replaced with a latex, silicone or rubber cover for gripping of the pushrod.

According to still another aspect of the present invention, the delivery device can be designed to accommodate or store more or less than 20 pellets.

According to still another aspect of the present invention, the needle can be made removable. In this aspect, a new needle can be pre-loaded with pellets and be replaced for reloading or reuse.

According to still another aspect of the present invention, the index wheel can be designed to rotate only in one direction.

According to still another aspect of the present invention, the pushrod track can be designed in a straight or curved manner, depending on the number of pellets required.

According to still another aspect of the present invention, the device of the present invention can be used to treat BPH, prostate cancer, prostitis, and other disease states occurring within a capsular membrane-confined organs, by administering viscous liquids, semi-solid or solid dosage forms which comprise chemical ablation agents (e.g., salts, basic agents, acidic agents, tissue necrosing enzymes, free-radical generating agents and oxidizing agents) in a concentrations effective to cause necrosis of the tissue.

The device disclosed herein can also be used to treat SUI and other conditions by injection of bulking agents. The bulk agent can be in the form of pellets, which require no gel carrier for delivery. The pellets are biocompatible and large enough not to migrate. Bulking therapy for SUI involves the injection of a material into tissue surrounding the urethra. This procedure, which can be done on an out-patient basis, tightens the seal of the sphincter by adding bulk to the surrounding tissue resulting in an increase in resistance to the flow of urine. This is accomplished by promoting reapposition of the urethral mucosa.

SUMMARY

Although various embodiments are specifically illustrated and described herein, it will be appreciated that modifications and variations of the invention are covered by the above teachings and are within the purview of the appended claims without departing from the spirit and intended scope of the invention. While the above has been discussed mainly in reference to dispensing solid formulations or pellets, gas and liquids can also be dispensed using the above apparatus methods. Furthermore, these examples should not be interpreted to limit the modifications and variations of the invention covered by the claims but are merely illustrative of possible variations.

What is claimed is:

1. An apparatus for delivering a pellet formulation into a body comprising:
   a cannula including an insertion end for insertion into the body and a channel to store the formulation comprising pellets abutted to each other end to end within the channel;
   a flexible rod to insert into an end of the cannula opposite the insertion end, the flexible rod having one end to contact the pellet formulation and having another end; and
   an index wheel that rotates about an axis that advances the flexible rod in length increments to advance the pellets through the channel of the cannula to deliver the formulation through the insertion end of the cannula, wherein at least part of the flexible rod is disposed about a curved track and the index wheel has one or more knobs and a toothed wheel coupled to the index wheel to engage the rod in the curved track and move the flexible rod laterally along the curved track in a predetermined distance upon rotation of one or more knobs of the index wheel by the operator; and
   a body in which the index wheel is disposed, wherein the body includes a plurality of windows disposed along the track, at least one of which windows is marked to indicate a number of units that remain in the cannula, and the other end of the flexible rod is visible from outside the body via one of the plurality of windows.

2. The apparatus according to claim 1, wherein the index wheel moves the rod through the channel of the cannula in a predetermined length increment that matches the length increment of one or more units of the formulation.

3. The apparatus according to claim 1, wherein the formulation comprises one or more units having a predetermined shape.

4. The apparatus according to claim 3, wherein the predetermined shape of the units of the formulation comprises one of the following: a cylinder, a sphere, a rectangular parallelepiped, a cuboid, a semiregular polyhedron, a convex polyhedron, a prism, and a wedge.

5. The apparatus according to claim 3, wherein the units of the formulation comprise radioactive seeds for brachytherapy.

6. The apparatus according to claim 1, wherein the cannula includes at least one of an echogenic and radiopaque tip for use with ultrasound or fluoroscopic applications.

7. The apparatus according to claim 1, wherein the cannula is flexible and sized to be used in a working channel of a scope.

8. The apparatus according to claim 1, wherein the formulation includes one of the following: a liquid, a solid, a gas, a dissolvable capsule, and a drug filled capsule.

9. The apparatus according to claim 1, wherein each of the units of the formulation comprise a pellet having a point at one end.

10. The apparatus according to claim 1, wherein the cannula stores more than two units of the formulation.

11. The apparatus according to claim 1, wherein a predetermined rotation of the index wheel causes a predetermined rotation of the toothed wheel to move the rod in the track in a lateral distance equal to one or more units of the formulation.

12. The apparatus according to claim 11, wherein the predetermined rotation comprises: one turn, a ½ turn, a ⅓ turn, a ¼ turn, and a ⅛ turn.

13. The apparatus according to claim 1, wherein at least one end of the rod is colored to increase visibility through the windows.

14. The apparatus according to claim 1, further comprising a dial to indicate a number of units that remain in the cannula.

15. The apparatus according to claim 1, further comprising a counter to indicate a number of units that remain in the cannula.

16. The apparatus according to claim 1, wherein the toothed wheel includes a cover being comprised of a material designed to grip the rod.

17. The apparatus according to claim 16, wherein the cover comprises a material including one of the following: latex, silicone, and rubber.

18. The apparatus according to claim 1, wherein the index wheel rotates only in one direction.

19. The apparatus according to claim 1, wherein the insertion end is sharpened.

20. The apparatus according to claim 1, wherein the formulation comprises one or more pellets.

* * * * *

UNITED STATES PATENT AND TRADEMARK OFFICE
CERTIFICATE OF CORRECTION

PATENT NO.         : 7,335,155 B2                                            Page 1 of 1
APPLICATION NO.    : 10/940274
DATED              : February 26, 2008
INVENTOR(S)        : Michael S. H. Chu It is certified that error appears in the above-identified patent and that said Letters Patent is hereby corrected as shown below:

Title Page (57) Abstract, Line 2, after "integer", change "amounts includes" to

-- amounts, including: --.

Specification, Col. 3, Line 51, after "or", change "translating" to -- translates --.

Specification, Col. 3, Line 55, after "motion", insert -- , --.

Specification, Col. 3, Line 56, after "preferred", insert -- , --.

Specification, Col. 4, Line 30, after "pushrod", insert -- , --.

Specification, Col. 4, Line 40, before "can", change "pellet" to -- pellets --.

Specification, Col. 4, Line 66, after "within", delete -- a --.

Specification, Col. 5, Line 3, after "a", change "concentrations" to -- concentration --.

Signed and Sealed this

Seventeenth Day of June, 2008

JON W. DUDAS
*Director of the United States Patent and Trademark Office*